United States Patent [19]

König et al.

[11] Patent Number: 5,596,064

[45] Date of Patent: Jan. 21, 1997

[54] POLYISOCYANATES BLOCKED WITH A MIXTURE OF BLOCKING AGENTS

[75] Inventors: Eberhard König, Leverkusen; Theodor Engbert, Köln, both of Germany

[73] Assignee: Bayer Aktiengesellschaft, Leverkusen, Germany

[21] Appl. No.: 430,775

[22] Filed: Apr. 27, 1995

[30] Foreign Application Priority Data

May 13, 1994 [DE] Germany ................. 44 16 750.4

[51] Int. Cl.$^6$ ................................. C08G 18/80
[52] U.S. Cl. ............. 528/45; 252/182.2; 252/182.21; 252/182.22; 548/266.8; 548/369.7
[58] Field of Search ............ 252/182.2, 182.21, 252/182.22; 548/266.8, 369.7; 528/45

[56] References Cited

U.S. PATENT DOCUMENTS

| | | | |
|---|---|---|---|
| 3,248,398 | 4/1966 | Mühlbauer et al. | 548/361 |
| 4,482,721 | 11/1984 | Wegner et al. | 548/262 |
| 4,976,837 | 12/1990 | Hughes et al. | 204/181.7 |
| 5,216,078 | 6/1993 | Cook et al. | 525/124 |
| 5,246,557 | 9/1993 | Hughes et al. | 204/181.4 |
| 5,352,755 | 10/1994 | Hughes et al. | 528/45 |
| 5,370,908 | 12/1994 | O'Connor et al. | 528/45 |

*Primary Examiner*—Rachel Johnson
*Attorney, Agent, or Firm*—Joseph C. Gil; Thomas W. Roy

[57] ABSTRACT

Blocked polyisocyanates containing aliphatically and/or cycloaliphatically bound isocyanate groups blocked by a mixture of blocking agents containing A) 30 to 70 equivalent % of 1,2,4-triazole, B) 30 to 70 equivalent % of 3,5-dimethylpyrazole, and C) 0 to 30 equivalent % of other blocking agents, a method of preparing these blocked polyisocyanates by blocking the isocyanate groups of a (cyclo)aliphatic polyisocyanate, wherein up to 20 NCO equivalent % of the isocyanate groups may optionally be reacted with compounds containing carboxylic acid hydrazide groups and isocyanate-reactive groups, and the use of the blocked polyisocyanates as crosslinking agents for organic polyhydroxyl compounds in one-component polyurethane stoving compositions.

3 Claims, No Drawings

POLYISOCYANATES BLOCKED WITH A MIXTURE OF BLOCKING AGENTS

BACKGROUND OF THE INVENTION

1. Field of the Invention

This present invention relates to new polyisocyanates blocked with a mixture of blocking agents, to a method for their production and to their use in one-component polyurethane stoving compositions which can be stoved at comparatively low temperatures of 120°–140° C. and which exhibit significantly reduced thermal yellowing.

2. Description of the Prior Art

Multilayer coating systems which have a clear, glossy coating and are based on blocked polyisocyanates and organic polyhydroxyl compounds, for example polyhydroxy polyacrylates, as the top coat, are becoming increasingly important due to their excellent industrial finishing properties, particularly for coating automobiles.

Polyisocyanates which are suitable for this special field of application must, in particular, (i) be capable of crosslinking at a maximum stoving temperature of 140° C., (ii) exhibit on very slight thermal yellowing during the stoving operation, and preferably exhibit no thermal yellowing at all, (iii) have a viscosity in concentrated organic solution which is sufficiently low for "high solids" applications, and (iv) be based on inexpensive raw materials.

Polyisocyanates blocked with 1,2,4-triazole according to EP-B 0,004,571, which have been described, in particular, as crosslinking agents for powder coatings, are essentially unsuitable for use in solvent containing coating compositions, because their solutions in organic solvents have comparatively high viscosities and are often unstable due to the tendency of the blocked polyisocyanates to crystallize.

Surprisingly, it has now been found that the abovementioned conditions can be fulfilled in an optimum manner if, instead of pure 1,2,4-triazole, a combination of this blocking agent with 3,5-dimethylpyrazole, and optionally other blocking agents known in the art, is used for blocking lacquer polyisocyanates.

Both 1,2,4-triazole and 3,5-dimethylpyrazole have been described as blocking agents for isocyanate groups, e.g, they are both disclosed in U.S. Pat. No. 3,248,398 as blocking agents for long chain aliphatic monoisocyanates. In addition, 3,5-dimethylpyrazole is described in addition to other pyrazoles as a blocking agent for organic polyisocyanates in EP-A-0,159,117. These blocked polyisocyanates are intended in particular for use as components of electrodeposition lacquers, which are generally recoated, so that the thermal stability of these primer coats is not a problem. This prior publication also contains no reference to the suitability of this blocking agent for the preparation of blocked polyisocyanates having a high thermal stability.

SUMMARY OF THE INVENTION

The present invention relates to blocked polyisocyanates which contain aliphatically and/or cycloaliphatically bound isocyanate groups, wherein at least 95 % of the isocyanate groups are blocked by a mixture of blocking agents containing A) 30 to 70 equivalent % of 1,2,4-triazole,
B) 30 to 70 equivalent % of 3,5-dimethylpyrazole, and
C) 0 to 30 equivalent % of one or more blocking agents which are different from A) and B), wherein the preceding percentages are based on the total equivalents of blocking agents and add up to 100, and which have a total content of blocked and non-blocked isocyanate groups (calculated as NCO) of 5 to 25 weight %, based on the solids content of the blocked polyisocyanates.

The present invention also relates to a process for preparing a blocked polyisocyanate which comprises
a) reacting at least 95% of the isocyanate groups, which are not reacted in step b), of a polyisocyanate component, optionally dissolved in lacquer solvents, and containing at least one polyisocyanate having (cyclo)aliphatically bound isocyanate groups and an isocyanate content of 7 to 30 weight % with a mixture of blocking agents containing A) 30 to 70 equivalent % of 1,2,4-triazole,
B) 30 to 70 equivalent % of 3,5-dimethylpyrazole, and
C) 0 to 30 equivalent % of at least one additional blocking agent which is different from A) and B),
   wherein the blocking agents are reacted in any sequence or as a mixture, and b) optionally reacting prior to, during or after the blocking reaction of step a), up to 20 equivalent % of said isocyanate groups with one or more compounds having at least one carboxylic acid hydrazide group and at least one isocyanate-reactive group such that the resulting blocked polyisocyanate contains up to 5 weight %, based on solids, of chemically incorporated structural units corresponding to the formula

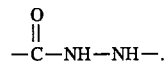

Finally, the present invention relates to a one-component polyurethane stoving composition containing these blocked polyisocyanates as crosslinking agents for organic polyhydroxyl compounds.

DETAILED DESCRIPTION OF THE INVENTION

The polyisocyanates which may be used to prepare the blocked polyisocyanates according to the invention are selected from known lacquer polyisocyanates having aliphatically and/or cycloaliphatically bonded isocyanate groups and an isocyanate content of 7 to 30 weight %, preferably 12 to 25 weight %. Lacquer polyisocyanates which are particularly suitable include those which contain biuret, isocyanurate and/or uretdione groups and are prepared from 1,6-diisocyanatohexane (HDI), 1-isocyanato-3,3,5-trimethyl-5-isocyanatomethylcyclohexane (IPDI) and/or 4,4'-diisocyanatodicyclohexyl methane. Lacquer polyisocyanates containing isocyanurate groups and based on (i) IPDI, (ii) mixtures of IPDI and 4,4'-diisocyanatodicyclohexyl methane or (iii) 1,6-diisocyanatohexane are particularly preferred.

1,2,4-triazole is used as blocking agent A), and 3,5-dimethylpyrazole is used as blocking agent B). 1,2,4-triazole is commercially available. 3,5-dimethylpyrazole can be obtained by the condensation of equimolar amounts of acetylacetone and hydrazine hydrate and removal of the water of reaction and hydration by means of toluene, for example.

Other blocking agents C), which may be used in conjunction with, but which are different from blocking agents A) and B), include oximes such as butanone oxime, secondary amines such as diisopropylamine or imidazole, acidic CH compounds such as diethyl malonate, and ε-caprolactam, for example, are suitable as further blocking agents C) which can optionally be used in conjunction.

According to a preferred embodiment of the method according to the invention, the polyisocyanate starting materials may be reacted before, during and/or after the blocking reaction with up to 20 equivalent %, preferably 1 to 12 equivalent % of compounds which contain at least one structural unit of formula

per molecule, and which contain at least one group which is capable of reacting with isocyanate groups and which is different from the said structural unit. The preceding percentage are based on the isocyanate groups of the polyisocyanate starting materials and on the groups of the hydrazine adduct which are capable of reacting with isocyanate groups. In addition, the quantitative ratio of the reactants for this modification are preferably selected so that the blocked polyisocyanates according to the invention contain up to 5 weight % of structural units corresponding to the preceding formula.

Examples of hydrazine adducts which are suitable for this modification reaction include those of formula

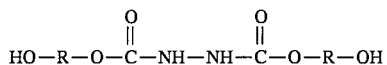

wherein
R represents an ethylene, isopropylene or 1,3-neopentylene radical.

The hydrazine adducts may be obtained, for example, by the reaction of 1 mole of hydrazine hydrate with 2 moles of a cyclic carbonate, e.g. ethylene, isopropylene or 1,3-neopentylene carbonate, in boiling toluene for example. The water of hydration and reaction are azeotropically distilled off during the course of preparation.

Examples of other hydrazine adducts which are suitable for the modification reaction according to the invention include the compounds cited in U.S. Pat. No. 5,216,078 (herein incorporated by reference), particularly the hydrazine adduct corresponding to the formula

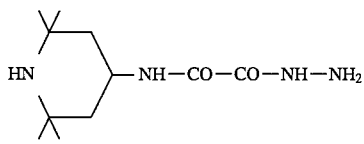

sold by Elf-Atochem under the trade name Luchem HA-R 100.

Blocking agents A) to C) are used for carrying out the method according to the invention in amounts such that the equivalent ratio of the isocyanate groups of the polyisocyanate starting materials, less the NCO groups optionally required for incorporating the hydrazine adduct, to the isocyanate-reactive groups of the blocking agent is 0.95:1 to 1.1:1. Accordingly, at least 95% of the isocyanate groups, preferably all the isocyanate groups, of the polyisocyanates are blocked.

In general, the method according to the invention is carried out at a temperature of 50° to 120° C., preferably 60 to 100° C., either in the absence of solvent or in suitable solvents, such as n-butyl acetate, methoxypropyl acetate or toluene, or in mixtures of higher aromatic solvents, such as those sold by Exxon under the trade name Solvesso.

In accordance with a preferred embodiment of the method according to the invention the dissolved isocyanate component is introduced and then a portion of the blocking agent, for example component A), is added. The reaction with 1,2,4-triazole is conducted at 100° C. for about 1 hour until the calculated NCO content is obtained. The mixture is then cooled, e.g. to 60° C., and is reacted with the more reactive component B), preferably until an NCO content can no longer be detected by IR spectroscopy. Finally, the product is optionally adjusted to the desired viscosity with solvent.

If the blocked polyisocyanates according to the invention are additionally modified by the incorporation of hydrazine adducts, they can be incorporated at any time before, during or after the blocking reaction. For example, when the aforementioned hydrazine adducts containing hydroxyl groups are used, these may be added to the reaction mixture after blocking with blocking agent A) and before the use of blocking agent B).

The reaction sequence cited by way of example merely indicates the preferred mode of procedure. It is also possible to use a mixture of blocking agents A) and B) for blocking the polyisocyanate starting material. If additional blocking agents C) are employed, these may also be used at any time, optionally in admixture with blocking agent A) or blocking agent B) or with a mixture of these two blocking agents However, the aforementioned reaction sequence is preferred, because the object of these reactions is to have no surplus blocking agent in the product after the NCO groups have been blocked as completely as possible. Accordingly, the less reactive blocking agent is preferably reacted first and the more reactive blocking agent is reacted thereafter with the remaining residue of NCO groups.

The predominantly or completely blocked polyisocyanates according to the invention constitute valuable crosslinking resins for organic polyhydroxyl compounds in the manufacture of stoving finishes. In this connection, they can be used instead of the blocked polyisocyanates which have previously been used for this purpose. Suitable polyhydroxyl compounds for this purpose as well as further details relating to the manufacture and application of stoving finishes of this type can be obtained from the relevant literature. A particularly preferred area of application for the products according to the invention is their use as crosslinking agents for clear polyurethane stoving lacquers, which are used as top coats, particularly in multi-coat automobile coatings. In such coatings the known polyester polyols, polyacrylate polyols or mixtures thereof are preferably used as co-reactants for the blocked polyisocyanates according to the invention.

In the following examples all percentages are given in weight % unless indicated otherwise.

EXAMPLES

Example 1 (Comparison)

This example illustrates the blocking of a typical lacquer polyisocyanate based on 1,6-diisocyanatohexane with 1,2,4-triazole. This resulted in a product which was unusable because it crystallized.

| Batch composition | |
| --- | --- |
| 200.0 g (1.0 equivalent) | of a lacquer polyisocyanate containing isocyanurate groups and prepared from 1,6-diisocyanatohexane. NCO content 21%, viscosity about 3000 mPas at 23° C. |

-continued

| Batch composition | |
|---|---|
| 72.5 g (1.05 mole) | 1,2,4-triazole |
| 117.0 g | methoxypropyl acetate |
| 389.5 g (1.0 equivalent of blocked NCO groups) | |

Experimental

The lacquer polyisocyanate was dissolved in methoxypropyl acetate. The total amount of 1,2,4-triazole was added to the stirred solution at room temperature, followed by gradual heating to 100° C. The blocking agent went into solution during this heating procedure. The solution was stirred for a further hour at 100° C. After the NCO bands had disappeared from the IR spectrum, the solution was allowed to cool. The solution became turbid during this cooling stage, and complete crystallization occurred after standing overnight.

Example 2 (Comparison)

This example illustrates the blocking of a typical lacquer polyisocyanate based on IPDI with 1,2,4-triazole,. This resulted in a blocked lacquer polyisocyanate having a viscosity which was too high for high solid applications.

| Batch composition | |
|---|---|
| 350.0 g (1.0 equivalent) | of a lacquer polyisocyanate containing isocyanurate groups and prepared from IPDI, present as a 70% solution in solvent naphtha. NCO content 12%, viscosity about 150 mpas at 23° C. |
| 72.5 g (1.05 mole) | 1,2,4-triazole |
| 65.0 g | methoxypropyl acetate |
| 487.5 g (1.0 equivalent of blocked NCO groups) Calculated content of blocked NCO groups = 8.6% solids content: 65%. | |

Experimental

The lacquer polyisocyanate and methoxypropyl acetate were mixed and stirred. 1,2,4-triazole, which was present in the form of white flakes, was gradually added and the mixture was heated to 100° C. with stirring. After a reaction time of about 6 hours almost no NCO groups could be determined by IR spectroscopy. The mixture was allowed to cool, whereupon a clear, pale yellow solution of the blocked polyisocyanate was obtained. This 65 % solution had a viscosity of 60,000 mPas at 23° C.

Example 3 (according to the invention)

This example illustrates the mixed blocking according to the invention using the polyisocyanate based on 1,6-diisocyanatohexane described in Example 1. In contrast to Example 1, a liquid, noncrystalline blocked lacquer polyisocyanate was obtained.

| Batch composition | |
|---|---|
| 400.0 g (2.0 equivalents) | of the lacquer polyisocyanate from Example 1 |
| 69.0 g (1.0 mole) | 1,2,4-triazole |
| 96.0 g (1.0 mole) | 3,5-dimethylpyrazole |
| 242.0 g | methoxypropyl acetate |
| 807.0 g (2.0 equivalents of blocked NCO groups) | |

Experimental

The polyisocyanate and methoxypropyl acetate were mixed. Solid 1,2,4-triazole (white flakes) was added with stirring. The mixture was heated to 100° C., whereupon the 1,2,4-triazole went into solution. An NCO content of 5.5.% was measured (calculated: 5.9 %) after a reaction time of 30 minutes. The mixture was cooled to 70° C. and 3,5-dimethylpyrazole (in the form of colorless crystals) was added in portions. After a reaction time of 30 minutes at 70° C., an NCO content could no longer be detected by IR spectroscopy. A clear, light yellow 70% solution was obtained, which had a viscosity of about 3000 mPas at 23° C. The dissolved blocked polyisocyanate had a content of blocked polyisocyanate groups (calculated as NCO and based on solids) of 14.8%. The properties of a clear coating produced from this polyisocyanate are described in Example 5.

Example 4 (according to the invention)

This example illustrates the mixed blocking according to the invention of the lacquer polyisocyanate based on IPDI described in Example 2. In contrast to Example 2, a blocked polyisocyanate with a relatively low viscosity was obtained.

| Batch composition | |
|---|---|
| 700.0 g (2.0 equivalents) | of the lacquer polyisocyanate from Example 2 |
| 69.0 g (1.0 mole) | 1,2,4-triazole |
| 96.0 g (1.0 mole) | 3,5-dimethylpyrazole |
| 143.0 g | methoxypropyl acetate |
| 1008.0 g (2.0 equivalents of blocked NCO groups) | |

Experimental

The polyisocyanate and methoxypropyl acetate were mixed. Solid 1,2,4-triazole (white flakes) was added with stirring. The mixture was heated to 100° C., whereupon the 1,2,4-triazole went into solution. An NCO content of 4.4.% was measured (calculated: 5.9 %) after a reaction time of about 30 minutes at 100° C. The mixture was cooled to 70° C. and 3,5-dimethylpyrazole (in the form of colorless crystals) was added. After a reaction time of 30 minutes at 70° C., an NCO content could no longer be detected by IR spectroscopy. A clear, pale yellow 65% solution was obtained, which had a viscosity of about 12,000 mPas at 23° C. The dissolved blocked polyisocyanate had a content of blocked polyisocyanate groups (calculated as NCO and based on solids) of 12.8%. The properties of a clear coating produced from this polyisocyanate are described in Example 5.

Example 5 (according to the invention)

This example illustrates clear coating compositions containing the blocked crosslinking agents from Examples 3 and 4 according to the invention, and also illustrates their thermal yellowing properties.

1. Clear coating composition preparation

The following polyol components, i.e., a "hard" acrylate and a "flexibility inducing" polyester, were used to produce clear compositions:

| 80 OH equivalent % | acrylate 1 | 290 g |
|---|---|---|
| 20 OH equivalent % | polyester 1 | 90 g |
| 100 OH equivalent % | 1 equivalent of OH component | 380 g |

Acrylate I was a 75% solution in xylene of a commercially available polyacrylate resin having a hydroxyl group content of the solution of 4.7% (Desmophen A TP LS 2051 manufactured by Bayer AG, Leverkusen).

Polyester I was an 80% solution in n-butyl acetate of a commercially available, branched polyester polyol (Desmophen TP LS 2971 manufactured by Bayer AG, Leverkusen). The hydroxyl group content of the solution was 3.8%.

Clear lacquers were produced by mixing the preceding polyol (acrylate/polyester) component with the crosslinking agents of Examples 3 and 4 according to the invention in an NCO/OH equivalent ratio of 1 and with the addition of a catalyst as set forth below.

| Clear coating composition | Poly-isocyanate | Acrylate/polyester polyol mixture | 0.1% dibutyl-tin dilaurate catalyst |
|---|---|---|---|
| A | Example 3 403 g | 380 g | 0.8 g |
| B | Example 4 504 g | 380 g | 0.9 g |

2. Application and thermal yellowing

The preceding clear coating compositions were applied to test panels which were coated with a commercially available white base coat ("Permacron Mischlack Serie 293 MB 501 Weiβ" manufactured by Spies & Hecker Cologne), to give a wet film thickness of about 120 to 150 μm.

The test panels were then stoved for 30 minutes at 140° C. in a drying oven. Thereafter the first color measurement was made by the CIE-LAB method (DIN 6174). The higher the positive b value determined by this method, the more the clear coating has discolored.

This was followed by the final overfiring operation which was effected for 30 minutes at 160° C. The increase in the yellow coleration, the so-called Δb value according to the CIE-LAB color system, was then measured. This value should be as close as possible to 0 for clear lacquers which are resistant to overfiring.

The results for clear coatings A and B were as follows:

| Clear laquer | Thermal yellowing after the stoving operation | Thermal yellowing after the overfiring operation (Δb) | Film thickness (μm) |
|---|---|---|---|
| A | 1.4 | 1.0 | 55 |
| B | −0.2 | 0.0 | 55 |

The results indicate that clear coating B exhibits practically no yellowing. For clear coating A) the sum of the individual values b) and Δb) is 2.4.

For comparison purposes an additional clear coating composition C) was prepared. The only difference between coating composition C) and coating composition A) was that the comparison composition contained a polyisocyanate blocked with butanone oxime. The polyisocyanate was the same polyisocyanate used to prepare the blocked polyisocyanate present in coating composition A), i.e., the polyisocyanate described in Example 1. The coating composition was cured using the procedure set forth above and the yellowness values were determined using the CIE-LAB method. The sum of the b+Δb values was 5.1, which is substantially higher than the value obtained for coating composition A).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A blocked polyisocyanate which contains aliphatically and/or cycloaliphatically bound isocyanate groups, wherein at least 95% of the isocyanate groups are blocked by a mixture of blocking agents containing A) 30 to 70 equivalent % of 1,2,4-triazole,
   B) 30 to 70 equivalent % of 3,5-dimethylpyrazole, and
   C) 0 to 30 equivalent % of one or more blocking agents which are different from A) and B),
      wherein the preceding percentages are based on the total equivalents of blocking agents and add up to 100, and which has a total content of blocked and non-blocked isocyanate groups (calculated as NCO) of 5 to 25 weight %, based on the solids content of the blocked polyisocyanate.

2. A process for preparing a blocked polyisocyanate which comprises a) reacting at least 95% of the isocyanate groups, which are not reacted in step b), of a polyisocyanate component, optionally dissolved in lacquer solvents, and containing at least one polyisocyanate having (cyclo)aliphatically bound isocyanate groups and an isocyanate content of 7 to 30 weight % with a mixture of blocking agents containing
      A) 30 to 70 equivalent % of 1,2,4-triazole,
      B) 30 to 70 equivalent % of 3,5-dimethylpyrazole, and
      C) 0 to 30 equivalent % of at least one additional blocking agent which is different from A) and B),
      wherein the blocking agents are reacted in any sequence or as a mixture, and b) optionally reacting prior to, during or after the blocking reaction of step a), up to 20 equivalent % of said isocyanate groups with one or more compounds having at least one carboxylic acid hydrazide group and at least one isocyanate-reactive group such that the resulting blocked polyisocyanate contains up to 5 weight %, based on solids, of chemically incorporated structural units corresponding to the formula

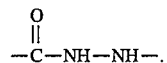

3. A one-component polyurethane stoving composition containing the blocked polyisocyanate of claim 1 and an organic polyhydroxyl compound.

* * * * *